United States Patent
Wang et al.

(10) Patent No.: US 8,822,184 B2
(45) Date of Patent: Sep. 2, 2014

(54) COLLECTIVE CHIRALITY OF BINARY PLASMONIC NANOPARTICLES JANUS ASSEMBLIES

(75) Inventors: Libing Wang, Wuxi (CN); Chuanlai Xu, Wuxi (CN); Liguang Xu, Wuxi (CN); Xiaoling Wu, Wuxi (CN)

(73) Assignees: Libing Wang, Wuxi (CN); Chuanlai Xu, Wuxi (CN); Liguang Xu, Wuxi (CN); Xiaoling Wu, Wuxi (CN)

( * ) Notice: Subject to any disclaimer, the term of this patent is extended or adjusted under 35 U.S.C. 154(b) by 0 days.

(21) Appl. No.: 13/462,612

(22) Filed: May 2, 2012

(65) Prior Publication Data

US 2013/0071882 A1    Mar. 21, 2013

(30) Foreign Application Priority Data

Sep. 15, 2011  (CN) .......................... 2011 1 0272660

(51) Int. Cl.
*C12P 19/34* (2006.01)
*B82Y 20/00* (2011.01)

(52) U.S. Cl.
CPC ................ *C12P 19/34* (2013.01); *B82Y 20/00* (2013.01); *Y10S 977/773* (2013.01); *Y10S 977/885* (2013.01)
USPC .......................... 435/91.52; 977/773; 977/885

(58) Field of Classification Search
None
See application file for complete search history.

(56) References Cited

U.S. PATENT DOCUMENTS 8,614,136 B1 * 12/2013 Cao et al. ...................... 438/409
2009/0258355 A1 * 10/2009 Maye et al. ........................ 435/6

OTHER PUBLICATIONS

Tan et al. Building plasmonic nanostructures with DNA, Nature Nanotechnology | vol. 6 | May 2011.*
Gu et al. Applied Physics B: Lasers and Optics (2010), 98(2-3), 353-363.*

* cited by examiner

*Primary Examiner* — Janet Epps-Smith
(74) *Attorney, Agent, or Firm* — Jacobson Holman PLLC; Jiwen Chen

(57) ABSTRACT

Multiple properties of plasmonic assemblies are determined by their geometrical organization. This patent focuses on the formation of Janus structure of the asymmetric assembly structure of the gold nanorods and gold nanoparticles. Chiral structure of gold nanorods and gold nanoparticles can be obtained through the characterization of optical spectra of the Janus structure. And it opens the door for the explanation of the mechanism of the chirality, plays a strong guiding role in the negative refractive material above and has good application prospects.

10 Claims, 3 Drawing Sheets

| | Sequence(5'-3') | Length |
|---|---|---|
| DNA1 (SEQ ID NO: 1) | PO$_4^{3-}$-CGTTAGGACTTACGCAAAAAAAAAA-SH | 25 |
| DNA2 (SEQ ID NO: 2) | TAACAATAATCCCTCAAAAAAAAAA-SH | 25 |
| DNA3 (SEQ ID NO: 3) | GAGGGATTATTGTTACGTTAGGACTTACGCA AAAAAAAAA-NH$_2$ | 40 |
| DNA4 (SEQ ID NO: 4) | GCGTAAGTCCTAACG-OH | 15 |

SEQUENCE LISTING

```
<160> NUMBER OF SEQ ID NOS: 4

<210> SEQ ID NO 1
<211> LENGTH: 25
<212> TYPE: DNA
<213> ORGANISM: Artificial Sequence
<220> FEATURE:
<223> OTHER INFORMATION: Synthesized
<220> FEATURE:
<221> NAME/KEY: misc_feature
<222> LOCATION: (1)...(1)
<223> OTHER INFORMATION: n is PO4/(3-)-cytosine
<220> FEATURE:
<221> NAME/KEY: misc_feature
<222> LOCATION: (25)...(25)
<223> OTHER INFORMATION: n is adenine-SH

<400> SEQUENCE: 1
ngttaggact tacgcaaaaa aaaan                                        25

<210> SEQ ID NO 2
<211> LENGTH: 25
<212> TYPE: DNA
<213> ORGANISM: Artificial Sequence
<220> FEATURE:
<223> OTHER INFORMATION: Synthesized
<220> FEATURE:
<221> NAME/KEY: misc_feature
<222> LOCATION: (25)...(25)
<223> OTHER INFORMATION: n is adenine-SH

<400> SEQUENCE: 2
taacaataat ccctcaaaaa aaaan                                        25

<210> SEQ ID NO 3
<211> LENGTH: 40
<212> TYPE: DNA
<213> ORGANISM: Artificial Sequence
<220> FEATURE:
<223> OTHER INFORMATION: Synthesized
<220> FEATURE:
<221> NAME/KEY: misc_feature
<222> LOCATION: (40)...(40)
<223> OTHER INFORMATION: n is adenine-NH2

<400> SEQUENCE: 3
gagggattat tgttacgtta ggacttacgc aaaaaaaaan                        40

<210> SEQ ID NO 4
<211> LENGTH: 15
<212> TYPE: DNA
<213> ORGANISM: Artificial Sequence
<220> FEATURE:
<223> OTHER INFORMATION: Synthesized
<220> FEATURE:
<221> NAME/KEY: misc_feature
<222> LOCATION: (15)...(15)
<223> OTHER INFORMATION: n is guanine-OH

<400> SEQUENCE: 4
gcgtaagtcc taacn                                                   15
```

COLLECTIVE CHIRALITY OF BINARY PLASMONIC NANOPARTICLES JANUS ASSEMBLIES

The present application claims the priority of Chinese Application No. 201110272660.1, filed Sep. 15, 2011 under 35 U.S.C. §119, which is hereby incorporated by reference.

TECHNICAL FIELD

The present invention relates to nanoparticle assembly and the intense optical property of these superstructures. Specifically, the invention relates to collective chirality of binary plasmonic nanoparticles Janus assemblies.

BACKGROUND OF THE INVENTION

In recent years, the gold nanomaterial assemblies with specific shapes possess unique properties which are different from those of monodisperse gold nanomaterials and gold materials, making them extremely bright prospect. Therefore, the self-assemblies of gold nanomaterials attract widespread attentions of nano-scientists around the world. Gold nanomaterials mainly include gold nanoparticles and gold nanorods. These nanomaterials possess specific optical absorption, light scattering and Raman enhancement effects depending on the size and shape, which make these two nanoparticles the most widely used materials in the nanoscience and nanotechnology research field, especially the gold nanorods.

A single gold nanorod has two localized surface plasmon resonance peaks, which are a longitudinal plasmon resonance peak (near infrared or infrared region) and a transverse plasmon resonance peak (around 520 nm), due to the two resonant directions of conduction band electrons on the rod. And gold nanorods, with spatial geometry and chemical anisotropy, can achieve strong light absorptions in the visible or near infrared region by adjusting the aspect ratio of gold nanorods (the ratio of length to diameter of the gold nanorods). Theses unique properties make gold nanorods to be the excellent raw material for the controllable self-assembly, and then provide a good model for theoretical analysis of the self-assembly materials. Thus the physical and chemical properties of macroscopic materials can be better understood by studying nature of the controllable, dynamic self-assembled materials. Notably to mention, the spatial geometry and chemical anisotropy are the key factors for the nanomaterials to achieve controllable self-assembly.

Janus particle was proposed by De Gennes in 1991 for the first time in the Nobel award ceremony, in order to describe a particle with different spherical nature. The difference of this nature is mainly due to the different spherical geometry of the particle. And Janus particle now attracts extensive attention of the scientific community, due to its unique asymmetric structure and properties, making it strong application prospects. Recently, the preparation methods of Janus particle are mainly including microfluidic surface modification synthesis, topology selection, the template self-assembly synthesis, controllable phase separation, and controllable surface nucleation. Self-assembly of gold nanomaterials has very strong plasmon coupling effects, leading to the strong electromagnetic enhancements. And binary plasmonic self-assemblies show fascinating properties different from that of the two separate nanomaterials, really makes the assembly of nanoparticles Janus wonderful and brilliant. Surprisingly, there is no reported method that successfully achieve high-yield binary nanoparticle Janus assemblies yet. Therefore, it is particularly important to establish a method to obtain high-yield binary nanoparticles Janus assemblies.

SUMMARY OF THE INVENTION

Accordingly, one aspect of the present invention is directed to a method of preparing the asymmetrical DNA functionalized gold nanorods (Au NRs) coupling with the enzymatic ligation and the magnetic separation of the superstructures of Au NRs and magnetic NPs.

Another aspect of the present invention is directed to the formation of binary plasmonic nanoparticles Janus assemblies of Au NPs and Au NRs resulting in the hybridization of DNA1 (SEQ ID NO: 1) and DNA4 (SEQ ID NO: 4) strands.

A further aspect of the present invention is directed to the measurement chiral property of the formed binary Janus nanoparticle assemblies.

The present invention provides the fabrication of the chiral binary plasmonic nanoparticles assemblies, which involves the preparation of Au NPs and Au NRs, the modification of DNA with the Au NRs, Au NPs and magnetic nanoparticles, the formation of binary nanoparticles Janus assemblies. And the fabrication method comprises:

a) Gold nanoparticles are synthesized by reduction of $HAuCl_4$ using trisodium citrate;

b) Gold nanorods are prepared by a seed-mediated growth procedure;

c) The synthesized gold nanoparticles based on step a), couple with sulfydryl modified DNA to form the complexes of Au NP-DNA;

d) The prepared gold nanorods based on step b), are modified with DNA on the sides of Au NR;

e) Magnetic nanoparticles (MNP) conjugate with amino modified DNA by an EDC procedure;

f) The prepared Au NR-DNA complexes hybridize with MNP-DNA complexes, according to steps d) and e), forming the assembly of gold nanorods and magnetic nanoparticles;

g) After adding DNA4 (SEQ ID NO: 4) strand complementary to the remaining sequence of DNA3 (SEQ ID NO: 3) modified on the magnetic nanoparticles, the DNA ligase is added for asymmetric extension of DNA modified on the gold nanorods;

h) The gold nanorods are recovered through magnetic separation following the dissociation of superstructures of gold nanorods and magnetic nanoparticles formed in the step g) at the melting temperature;

i) Based on steps c) and h), the prepared Au NP-DNA complexes hybridize with Au NR-DNA complexes to obtain binary plasmonic nanoparticles Janus assemblies;

j) The prepared binary nanoparticles Janus assemblies based on step i) are charactering by transmission electron microscopy (TEM), circular dichroism spectra (CD) as well as synchrotron small-angle X-ray scattering (S-SAXS).

BRIEF DESCRIPTION OF THE DRAWINGS

FIG. 5 shows a table listing the sequence and length of DNA involved in the present invention.

DETAILED DESCRIPTION OF THE INVENTION

Figure 1:
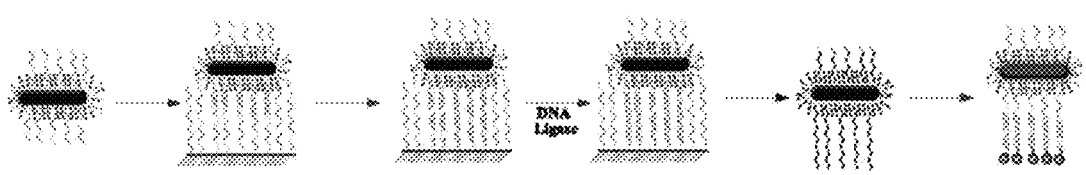
FIG. 1 is a schematic view illustrating the synthetic method for the binary plasmonic nanoparticle Janus assemblies.
Figure 2:
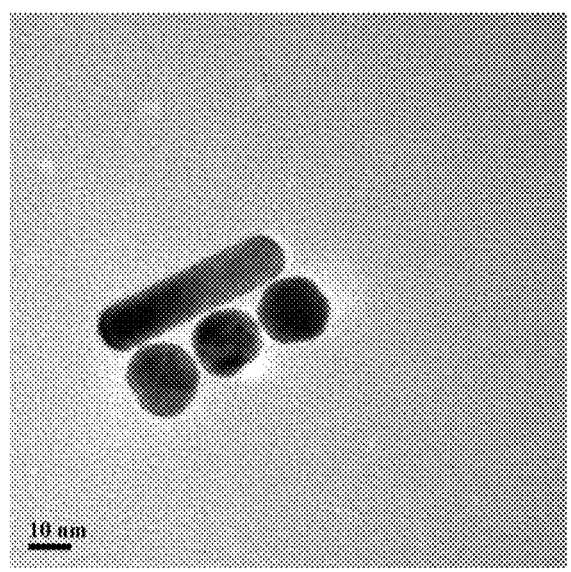
FIG. 2 shows the TEM images of the binary plasmonic NPs assemblies samples.
Figure 3:
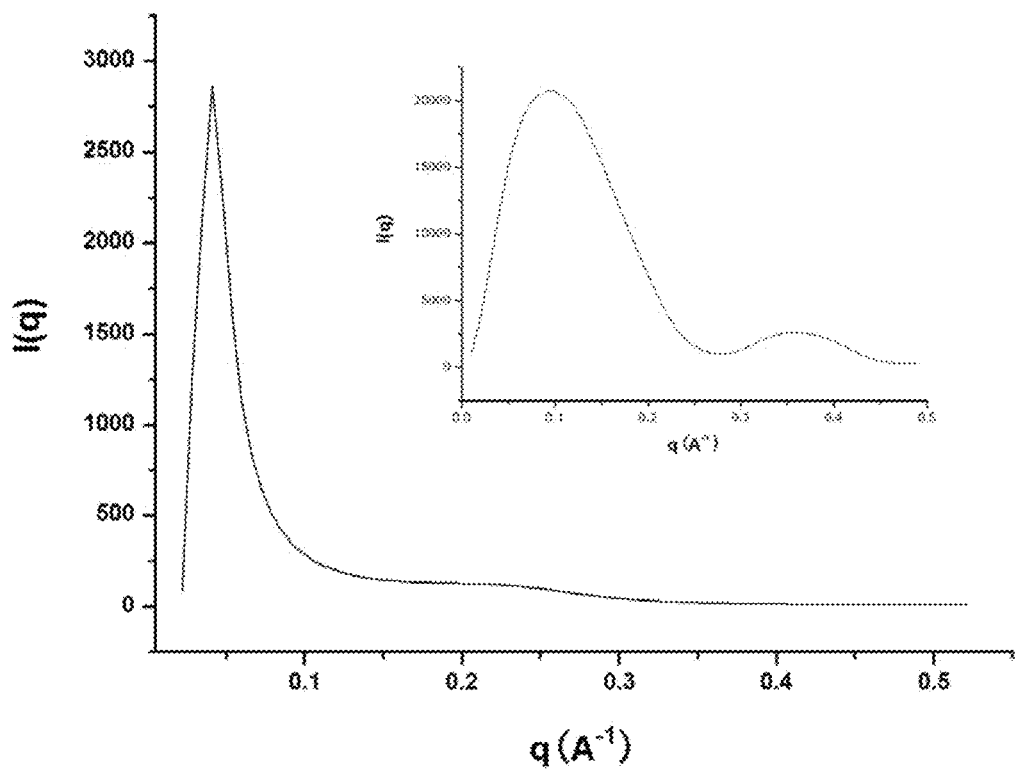
FIG. 3 shows S-SAXS experimental results and modeling patterns with scaling factor 0.2. (A: experimental results, the insert: amplification curve in the range of $0.021 \leq q \leq 0.1$; B: S-SAXS modeling patterns respectively.) The numbers in Angstroms in FIG. 2B means the main peak to confirm the relative size of the assemblies.
Figure 4:
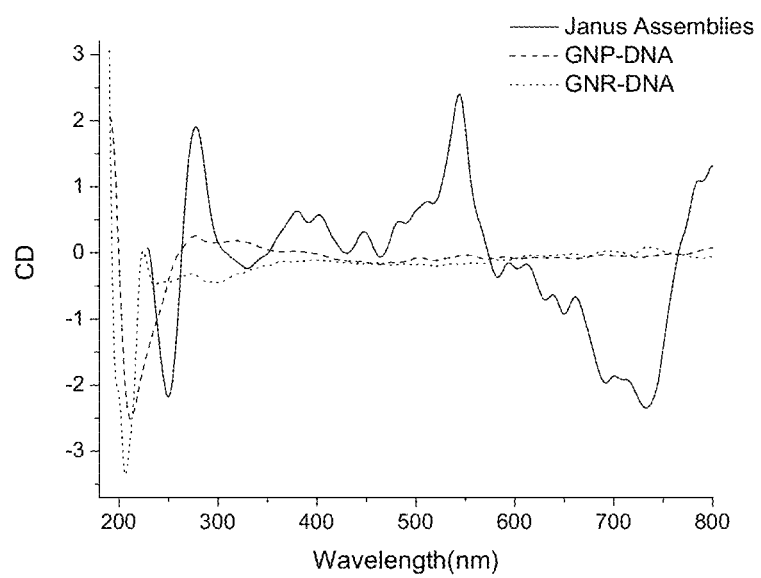
FIG. 4 illustrates the CD spectrum of binary plasmonic NPs Janus assemblies.

The detailed information of the invention is further described through the steps listed in the following text. All the reagents involved are analytical grade purify. Notably to mention that the following detailed steps are as exemplifications, while the present invention is not limited to the content as follows:

Step 1: Synthesis of Gold Nanoparticles

Au NPs are synthesized by reduction of $HAuCl_4$ using trisodium citrate. Typically, an aqueous trisodium citrate solution (2.5 mL, 1% by weight, freshly prepared) is quickly added to a boiling aqueous solution of $HAuCl_4$ (100 mL, 0.25 mM) under vigorous stirring and reflux. After several minutes, the color of the solution changes from pale yellow to brilliant red. After boiling for 10 minutes, the heat source is removed to allow the reaction solution to cool to room temperature, diluting the solution to 100 mL, and it was subsequently stored at 4° C.

Step 2: The Synthesis of Gold Nanorods (1) Au NRs with an aspect ratio of approximately 3 are prepared by a seed-mediated growth procedure. Initially, a 2 g/L $HAuCl_4$ (0.1 mL) is added to 0.2 M CTAB solution (1 mL) that is kept at a constant temperature of 28.0° C. Immediately, a deep-orange solution is obtained. Then, freshly prepared 0.01M NaBH4 solution (0.12 mL) is added in one portion, and the solutions are mixed by inversion. After stirring rapidly for 2 min, the solution turns pale-brown in color.

(2) To prepare the Au NR, 2 g/L $HAuCl_4$ (5 mL) is mixed with 0.2 M CTAB solution (1 mL) and 4 mL of water. After that, 65 µL of 0.1 M ascorbic acid solution and 0.125 mL of 0.01M $AgNO_3$ solution are added to the reaction media followed by mixing for 2 min, which resulted in a colorless solution. Finally, 0.05 mL of the seed solution is added with gentle mixing for about 20 seconds. The Au NRs can be used after aging for 4 hours.

Step 3: Preparation of Single-Strand DNA-Modified Au NPs (1) The prepared Au NPs (10 mL) based on step 1, are centrifuged (10000 rpm) for 10 min, followed by dispersing the precipitate with 1 mL of 0.01 M pH 8.0 phosphate buffers, while maintaining a SDS concentration of 0.01%. It is stored at 4° C. before application.

(2) DNA1 oligomers (SEQ ID NO: 1) are added to Au NPs in 0.01 M phosphate buffer with 0.01% sodium dodecylsulfate (SDS). The solution of DNA1 and Au NP is incubated at room temperature for 20 min. The concentration of NaCl is increased to 0.05 M using 2 M NaCl and 0.01 M pH 8.0 phosphate buffers, while maintaining a SDS concentration of 0.01%. The solution of DNA and Au NP is then sonicated for 10 seconds followed by a 20 min incubation period at room temperature. This process is repeated for one more increment of 0.01 M NaCl and for every 0.1 M NaCl increment thereafter until a concentration of 0.4 M NaCl is reached. The ionic strength adaptation process was followed by incubation overnight at room temperature.

(3) To remove the excess of DNA1 (SEQ ID NO: 1), Au NPs are centrifuged, and the supernatant is removed, leaving a pellet of Au NPs at the bottom. The particles are then resuspended in 0.01% SDS. This washing process is repeated for one more time. The conjugate was stored at 4° C.

Step 4: Fabrication of Single-Strand DNA-Modified Au NRs

The prepared Au NRs (100 µL) based on step 1, is reacted with 10 µL of 10 µM DTT for 12 h, followed by addition of 40 µL of DNA2 (SEQ ID NO: 2) to modify the sides of Au NRs. After stirring for 12 h, the solution is centrifuged at 5000 rpm for 6 min. And the supernatant is removed. The precipitate particles are then resuspended in 100 µL of water. This washing process is repeated for one more time before storing at 4° C.

Step 5: Fabrication of Single-Strand DNA-Modified MNPs

Carboxyl-modified magnetic nanoparticles of 200 nm are synthesized through solvothermal method. A volume of 0.5 mL MNP prepared above, N-hydroxysuccinimide (NHS) (0.62 mg) and N-ethyl-N'-[(3-dimethylamino) Cyl] carbodiimide hydrochloride (EDC-HCl) (1.13 mg) are stirred for reaction at room temperature overnight, and then centrifugalize, remove the precipitate, add 15 µL 100 µM DNA3 (SEQ ID NO: 3) to the supernatant for reaction under stir at 4° C. overnight. After reaction, the solution is separated by the magnetic separation to remove the supernatant. Then add the PBST as the washing liquid, this washing process is repeated for one more time. Finally, resuspend in 1 mL of 0.02 mol/L pH 7.6 Tris buffer and stored at 4° C.

Step 6: Self-Assembly of Au NRs and MNPs

The prepared asymmetric modified gold nanorods 10 µL and magnetic nanoparticles-DNA3 (SEQ ID NO: 3) complex 50 µL are added into 60 µL pH7.5 0.01M Tris-HCl hybridization buffer, maintaining 0.01% SDS, 10 mM $MgCl_2$, and react for 12 hours under shake condition. Finally, the complex of gold nanorods and magnetic nanoparticles are separated using magnetic separation, removal of the free gold nanorods.

Step 7: Asymmetric Extension of DNA Modified on the Au NRs

A 4 µL of DNA4 (SEQ ID NO: 4) (100 µM) is added to complex assemblies of Au NRs and MNPs prepared in the above step 6, under stirring for 5 h at room temperature. And then, 1 µL ATP (100 µM) and T4 DNA ligase (4000 units of final enzyme activity/mL) are shaking for 5 h to allow for incubation. Finally, complexes of asymmetric extension modified DNA of Au NRs and MNPs after magnetic separation under the addition magnetic field.

Step 8: The Dissociation of Complexes of Au NRs and MNPs

The superstructure complexes of Au NRs and MNPs are dissociated due to incubation at 90° C. for 10 minutes. And then MNPs are removed through magnetic separation, the supernatant is centrifuged 8000 rpm for 10 minutes. Finally, the remained nanoparticles are resuspended in 10 µL of 0.01 M pH 8.0 phosphate buffer, maintaining 0.01% SDS, and stored at 4° C.

Step 9: Formation of Binary Plasmonic Nanoparticle Janus Assemblies

In order to form the binary Janus assemblies, 10 µL of asymmetric modified Au NRs are mixed with 50 µL of complex of Au NPs-DNA1 in 6 µL of 0.01 M Tris-HCl buffer (0.01% SDS, $MgCl_2$ 20 mM, pH 8.0). The mixture was incubated for 12 hours at room temperature.

Step 10: Structure Characterization and Simulation of Binary Plasmonic Nanoparticle Janus Assemblies (1) Following a 12-hour incubation of NPs and NRs resulting in the hybridization of DNA1 (SEQ ID NO: 1) and DNA4 (SEQ ID NO: 4) strands, NR and NP assemblies were structurally examined by transmission electron microscopy (TEM), circular dichroism (CD) spectra as well as synchrotron small-angle X-ray scattering (S-SAXS). The representative TEM images clearly demonstrate the conformations of the ensembles.

(2) To obtain detailed information about ensembles in solution, SAXS, as an indirect technique, can be used. Above the SAXS characterization experiments, there are two curves in the data: one is based on the gold nanorods and gold nanoparticles simply mixing without hybrid assembly, another one is based on the hybridization of gold nanorods and gold nanoparticles, forming Janus structures. In order to confirm the assembly of specific structures in solution, we utilized the "Forcite" module in Materials Studio 5.5 to perform SAXS calculations. The calculations were based on the intensities of each hid reflection:

$$I(hkl) = fn \cos 2(hxn+kyn+lzn)2 + fn \sin 2(hxn+kyn+lzn)2 \quad (1)$$

Where hkl is equivalent to the scattering vector (q), fn is the scattering factor of atom n, and xn, yn, zn are the fractional coordinates of atom n.

While the foregoing embodiments of the invention have been illustrated and described, it will be appreciated that various changes can be made therein without departing from the spirit and scope of the invention.

The embodiments of the invention in which and exclusive properties or privilege is claimed are defined as follows.

The invention claimed is:

1. A novel preparation method of nanoparticle Janus assemblies comprising the steps of:
   (1) synthesizing gold nanoparticle (SU NPs) by reduction of HAuCl$_4$ using trisodium citrate;
   (2) preparing gold nanorods (Au NRs) by seed-mediated growth procedure;
   (3) coupling the synthesized Au NPs with first sulfydryl modified single strand oligonucleotides of SEQ ID NO: 1 (DNA1) to form gold nanoparticle-DNA1 conjugate (Au NP-DNA1);
   (4) coupling the prepared Au NRs with second sulfydryl modified single strand oligonucleotides of SEQ ID NO: 2 (DNA2) to an outer surface of Au NR to form DNA2 conjugate (Au NR-DNA2);
   (5) conjugating magnetic nanoparticles (MNP) with third amino modified single strand oligonucleotides of SEQ ID NO: 3 (DNA3) by 1-ethyl-3-(3-dimethylaminopropyl) carbodiimide (EDC) procedure to form magnetic nanoparticles-DNA conjugates (MNP-DNA3), wherein the DNA2 is complementary to a first part of the DNA3;
   (6) hybridizing the prepared Au NR-DNA2 with MNP-DNA3 to form an assembly of the Au NR-DNA2 and MNP-DNA3;
   (7) after adding fourth single strand oligonucleotides of SEQ ID NO: 4 (DNA4) that is complementary to a second part of the DNA3 to hybridize DNA4 with DNA3 and form an assembly of Au NR-DNA2, DNA4 and MNP-DNA3, adding a DNA ligase to link the Au NR-DNA2 and the DNA4 in the assembly of Au NR-DNA2, DNA4 and MNP-DNA3;
   (8) dissociating the assembly of Au NR-DNA2, DNA4 and MNP-DNA3 formed in the step (7) at the melting temperature to free Au NR-DNA2-DNA4 from MNP-DNA3, then recovering the Au NR-DNA2-DNA4 through magnetic separation;
   (9) based on step (3) and (8), hybridizing the prepared Au NP-DNA1 with Au NR-DNA2-DNA4 to obtain binary plasmonic nanoparticles Janus assemblies;
   (10) characterizing the prepared binary nanoparticles Janus assemblies based on step (9) by transmission electron microscopy (TEM), circular dichroism spectra (CD) as well as synchotron small-angle X-ray scattering (S-SAXS).

2. The method of claim 1, wherein the synthesis of Au NPs comprises the following steps:
   adding an aqueous trisodium citrate solution (2.5 mL, 1% by weight, freshly prepared) to a boiling aqueous solution of HAuCl$_4$ (100 mL, 0.25 mM) under vigorous stirring and reflux;
   waiting for several minutes until the color of the solution changes from pale yellow to brilliant red;
   boiling the solution for 10 minutes;
   cooling the solution to room temperature;
   diluting the solution to 100 mL; and
   storing the solution at 4° C.

3. The method of claim 1, wherein the synthesis of Au NRs comprises the following steps:
   adding HAuCl$_4$ (0.1 mL, 2 g/L) to CTAB solution (1 mL, 0.2 M) at 28.0° C.;
   adding freshly prepared NaBH$_4$ solution (0.12 mL, 0.01 M) under vigorous stirring
   waiting for 2 minutes until the solution turns pale-brown in color to form a seed solution;
   adding HAuCl$_4$ (5 mL, 2 g/L) to a mixture of CTAB solution (1 mL, 0.2M) and 4 mL of water;
   adding ascorbic acid solution (65 µL, 0.1 M) and AgNO$_8$ solution (0.125 mL, 0.01 M) to a reaction media under vigorous stirring;
   waiting for 2 minutes until the solution turned into a colorless solution;
   adding the seed solution (0.05 mL) to the colorless solution and gentle mixing for about 20 seconds to obtain the Au NRs;
   aging the Au NRs for 4 hours.

4. The method of claim 1, wherein the preparation of single-strand DNA1-modified Au NPs comprises the following steps:
   adding DNA1 to Au NPs in 0.01 M phosphate buffer with 0.01% sodium dodecylsulfate (SDS) to form a mixture;
   allowing the mixture to react for about 20 minutes;
   allowing the mixture to be sonicated for about 10 seconds and reacted for about 20 minutes;
   removing the supernatant with centrifugation to purify Au NP-DNA1 and then resuspending the Au NP-DNA1 in 0.01% SDS; and
   storing the solution at 4° C.

5. The method of claim 1, wherein the fabrication of single-strand DNA2-modified Au NRs comprises the steps of:
   adding 10 µL of 10 µM dithiothreitol solution (DTT) to the Au NRs (100 µL) to form a mixture;
   allowing the mixture to react for 12 hours;
   adding 40 µL of DNA2 to the mixture;
   allowing the mixture to react for 12 hours;
   removing supernatant with centrifugation of Au NRs-DNA2 at 5000 rpm for 6 minutes;
   resuspending the Au NR-DNA2 with water; and
   storing the solution at 4° C.

6. The method of claim 1, wherein the fabrication of single-strand DNA3-modified MNPs comprises the steps of:
   adding N-hydroxysuccinimide (NHS) (0.62 mg) and N-ethyl-N'-[(3-dimethylamino) Cyl]carbodiimide hydrochloride (EDC-HCl) (1.13 mg) to 0.5 mL MNP;
   allowing the mixture to react at room temperature overnight under stirring;
   adding 15 µL 100 µM of DNA3 to the mixture for reaction under stirring at 4° C. overnight;
   separating the solution by the magnetic separation to remove the supernatant;
   resuspending MNP-DNA3 in 1 mL of 0.02 mol/L pH 7.6 Tris buffer and storing at 4° C.

7. The method of claim 1, wherein the self-assembly of Au NR-DNA2 and MNP-DNA3 comprises the steps of:
   adding Au NR-DNA2 (10 µL) and MNP-DNA3 (50 µL) to 60 µL pH7.5 0.01M Tris-HCl hybridization buffer, maintaining 0.01% SDS, 10 mM MgCl$_2$t to form a mixture;
   allowing the mixture to react for 12 hours under shake condition to form the assembly of Au NR-DNA2 and MNP-DNA3.

8. The method of claim 1, wherein the asymmetric extension of Au NR-DNA2 with DNA4 comprises the steps of:
   adding 4 µL of DNA4 (100 µM) to said assembly of Au NR-DNA2 and MNP-DNA3;
   allowing the mixture to react for 5 hours at room temperature;
   adding 1 µL ATP (100 µM) and T4 DNA ligase (4000 units of final enzyme activity/mL) to link DNA2 and DNA4;
   allowing the mixture to react for 5 hours under gentle shaking to form the assembly of Au NR-DNA2, DNA4 and MNP-DNA3;
   separating Au NR-DNA2-DNA4 with MNP-DNA3 under the addition magnetic field.

9. The method of claim 1, wherein the dissociation of assembly of Au NR-DNA2-DNA4 and MNP-DNA3 comprises:
- dissociating the assembly of Au NR-DNA2-DNA4 and MNP-DNA3 at 90° C. for 10 minutes;
- removing MNP-DNA3 with additional magnetic field;
- centrifuging the mixture to remove the supernatant at 8000 rpm for 10 minutes;
- resuspending the Au NR-DNA2-DNA4 with phosphate buffer (10 μL, 0.01 M, pH 8.0, and 0.01% SDS); and
- storing at 4° C.

10. The method of claim 1, wherein the formation of binary plasmonic nanoparticle Janus assemblies comprises the steps of:
- adding 10 μL of Au NR-DNA2-DNA4 and 50 μL of Au NP-DNA1 to 6 μL of 0.01 M Tris-HCl buffer (0.01% SDS, MgCl$_2$ 20 mM, pH 8.0); and
- allowing the mixture to react for 12 hours at room temperature to obtain the binary plasmonic nanoparticle Janus assemblies.

* * * * *